(12) United States Patent
Kobayashi (10) Patent No.: US 10,627,615 B2
(45) Date of Patent: Apr. 21, 2020

(54) ENDOSCOPE DISTAL END PORTION, ENDOSCOPE, AND OPTICAL ADAPTOR

(71) Applicant: OLYMPUS CORPORATION, Tokyo (JP)

(72) Inventor: Eiichi Kobayashi, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/980,075

(22) Filed: May 15, 2018

(65) Prior Publication Data

US 2019/0041627 A1    Feb. 7, 2019

(30) Foreign Application Priority Data

Aug. 7, 2017 (JP) .................................. 2017-152284

(51) Int. Cl.
  *G02B 23/24* (2006.01)
  *A61B 1/00* (2006.01)
  *A61B 1/06* (2006.01)

(52) U.S. Cl.
  CPC ...... *G02B 23/2423* (2013.01); *A61B 1/00096* (2013.01); *A61B 1/00101* (2013.01); *A61B 1/00105* (2013.01); *A61B 1/00177* (2013.01); *A61B 1/0615* (2013.01); *A61B 1/0623* (2013.01); *G02B 23/2469* (2013.01)

(58) Field of Classification Search
  CPC ............ G02B 23/2423; G02B 23/2469; A61B 1/00096; A61B 1/0623; A61B 1/0615; A61B 1/00105; A61B 1/00177; A61B 1/00101
  See application file for complete search history.

(56) References Cited

U.S. PATENT DOCUMENTS

| | | | | |
|---|---|---|---|---|
| 2013/0137923 | A1* | 5/2013 | Honda | G02B 23/2469 600/109 |
| 2014/0347878 | A1* | 11/2014 | Honda | G02B 23/2461 362/574 |
| 2017/0105608 | A1* | 4/2017 | Kura | A61B 1/04 |
| 2017/0215714 | A1* | 8/2017 | Shinji | A61B 1/04 |
| 2018/0092515 | A1* | 4/2018 | Yashiro | A61B 1/00096 |

FOREIGN PATENT DOCUMENTS

JP    H10-311954 A    11/1998

* cited by examiner

*Primary Examiner* — Kevin Quarterman
(74) *Attorney, Agent, or Firm* — Scully, Scott, Murphy & Presser, P.C.

(57) ABSTRACT

An endoscope distal end portion includes a longitudinal axis and is provided at a distal end of an insertion section, and the endoscope distal end portion includes an observation window provided on a side with respect to an insertion direction of the insertion section, an illumination window disposed on proximal end side of the observation window, and a reflector disposed on distal end side of the observation window to include a predetermined angle with respect to the longitudinal axis, and configured to reflect illumination light outputted from the illumination window, to a rear observation region.

6 Claims, 13 Drawing Sheets

ENDOSCOPE DISTAL END PORTION, ENDOSCOPE, AND OPTICAL ADAPTOR

CROSS REFERENCE TO RELATED APPLICATION

This application claims the benefit of Japanese Application No. 2017-152284 filed in Japan on Aug. 7, 2017, the contents of which are incorporated herein by this reference.

BACKGROUND

1. Technical Field

The present invention relates to an endoscope distal end portion, an endoscope, and an optical adaptor that allow for observation of a side or an oblique direction including a predetermined angle with respect to an insertion direction of an insertion section.

2. Background Art

An endoscope apparatus is conventionally widely used in an industrial field and a medical field. The endoscope apparatus typically includes an insertion section to be inserted into an object to be observed, and a main body section including a display section that displays an endoscope image as an observation image acquired by picking up an image in the object. In the industrial field, the endoscope apparatus is used for, for example, observation and inspection of internal damage and corrosion, through insertion of the elongated insertion section into a boiler, a turbine, and an engine.

Such an endoscope apparatus includes a well-known configuration that includes a bending portion to change a visual field direction, thereby allowing for front viewing of a desired direction, irrespective of the medical field and the industrial field.

The endoscope apparatus in the industrial field, however, cannot be changed in the visual field direction by the bending portion, for example, when damage and a shape of a connection part of conduits are inspected, in addition to inspection of a conduit with a small diameter and inspection of a hole diameter of the conduit. This does not allow for front viewing of a site to be inspected such as an inner surface of the conduit.

Therefore, for example, as disclosed in Japanese Patent Application Laid-Open Publication No. H10-311954, a technology of an endoscope that includes a prism or the like at the distal end portion to allow for observation of a side including an angle with respect to an insertion axis, is well-known.

In such an existing endoscope, a light guide fiber bundle is made parallel to the insertion direction, and illumination light is applied in a direction substantially orthogonal to an observation direction of the side including the angle with respect to the insertion direction. Further, a technology in which an inclined surface including light reflection function is provided to change the illumination direction to the observation direction has been disclosed.

SUMMARY

An endoscope distal end portion according to an aspect of the present invention includes a longitudinal axis and is provided at a distal end of an insertion section. The endoscope distal end portion includes an observation window provided on a side with respect to an insertion direction of the insertion section, an illumination window disposed on proximal end side of the observation window, and a reflector disposed on distal end side of the observation window to include a predetermined angle with respect to the longitudinal axis, and configured to reflect illumination light outputted from the illumination window, to a rear observation region.

An endoscope according to another aspect of the present invention includes an endoscope distal end portion that includes a longitudinal axis and is provided at a distal end of an insertion section. The endoscope distal end portion includes an observation window provided on a side with respect to an insertion direction of the insertion section, an illumination window disposed on proximal end side of the observation window, and a reflector disposed on distal end side of the observation window to include a predetermined angle with respect to the longitudinal axis, and configured to reflect illumination light outputted from the illumination window, to a rear observation region.

An optical adaptor according to an aspect of the present invention is detachably attachable to a distal end portion that includes a longitudinal axis and is provided at a distal end of an insertion section. The optical adaptor includes an observation window provided on a side with respect to an insertion direction of the insertion section, an illumination window disposed on proximal end side of the observation window, and a reflector disposed on distal end side of the observation window to include a predetermined angle with respect to the longitudinal axis, and configured to reflect illumination light outputted from the illumination window, to a rear observation region.

DETAILED DESCRIPTION OF THE PREFERRED EMBODIMENTS

An endoscope as the present invention is described below. Note that, in the following description, drawings based on each embodiment are schematic sketches, may not reflect actual relationship between a thickness and a width of each portion, actual thickness ratio of each portion, etc., and may include a part different in dimensional relationship or ratio between drawings.

First Embodiment

First, a configuration of an endoscope apparatus according to a first embodiment of the present invention is described.

Figure 1:
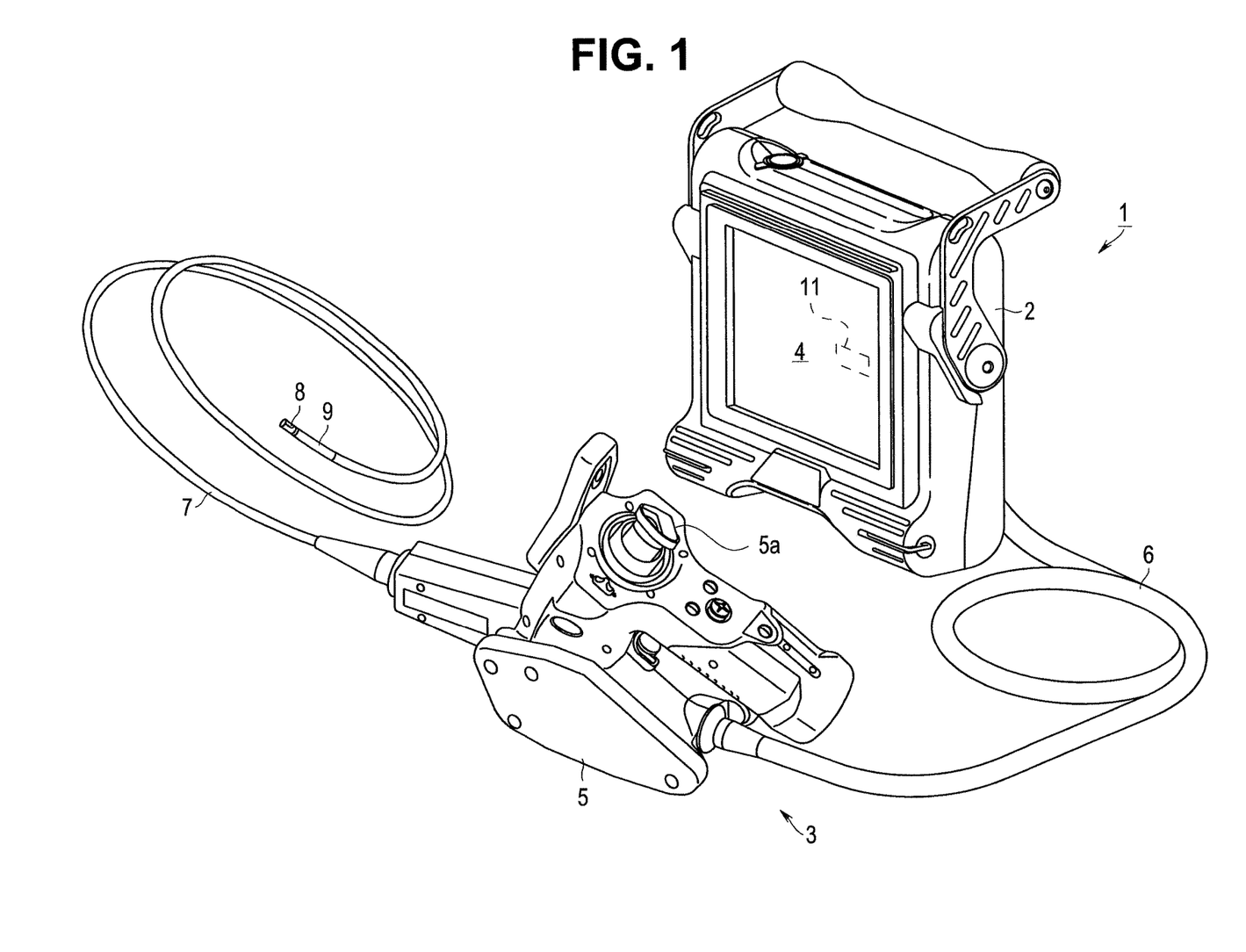
FIG. 1 is an external appearance configuration diagram of an endoscope apparatus according to an aspect.
Figure 2:
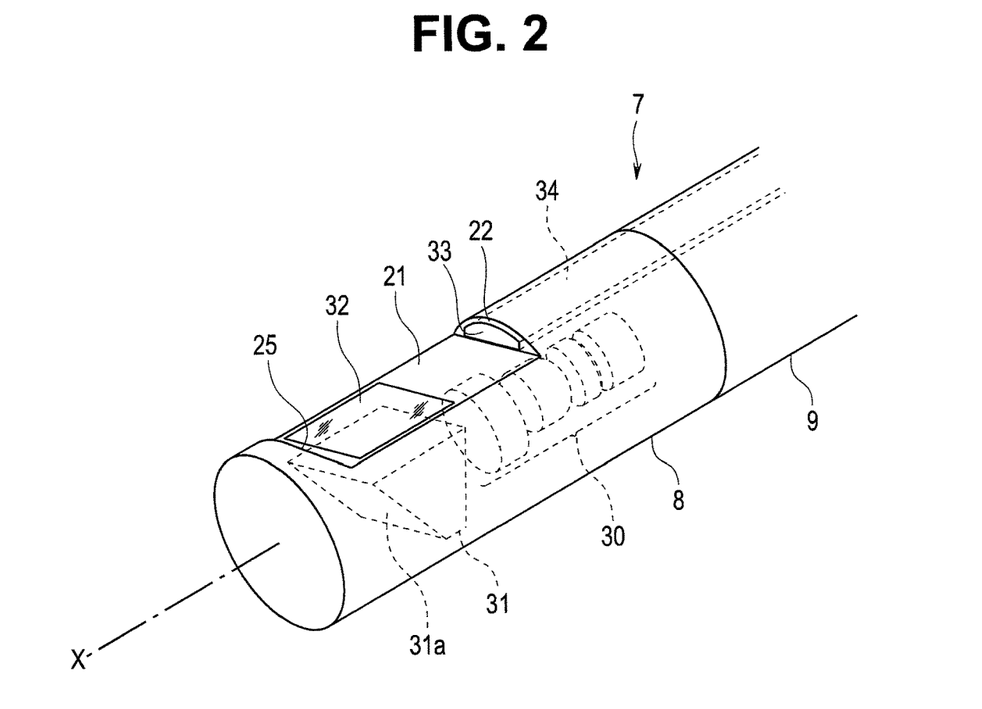
FIG. 2 is a perspective view illustrating a configuration of a distal end portion as viewed from distal end side, according to the aspect.
Figure 3:
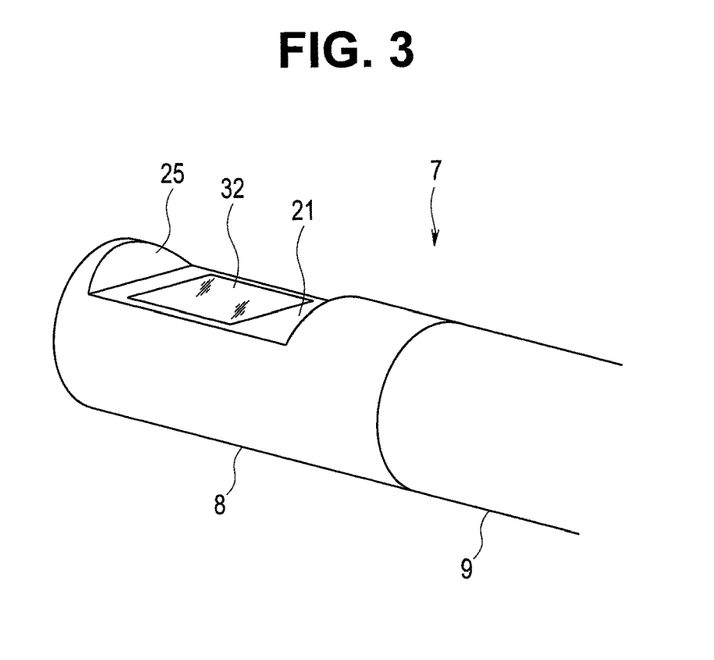
FIG. 3 is a perspective view illustrating the configuration of the distal end portion as viewed from proximal end side, according to the aspect.
Figure 4:
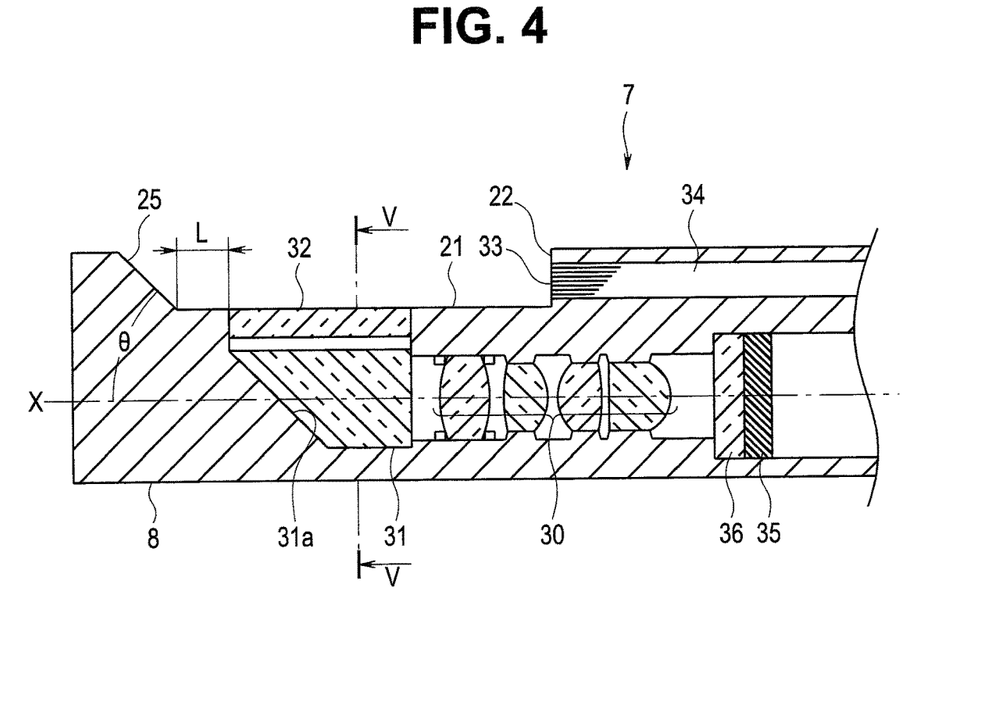
FIG. 4 is a cross-sectional view illustrating the configuration of the distal end portion, according to the aspect.
Figure 5:
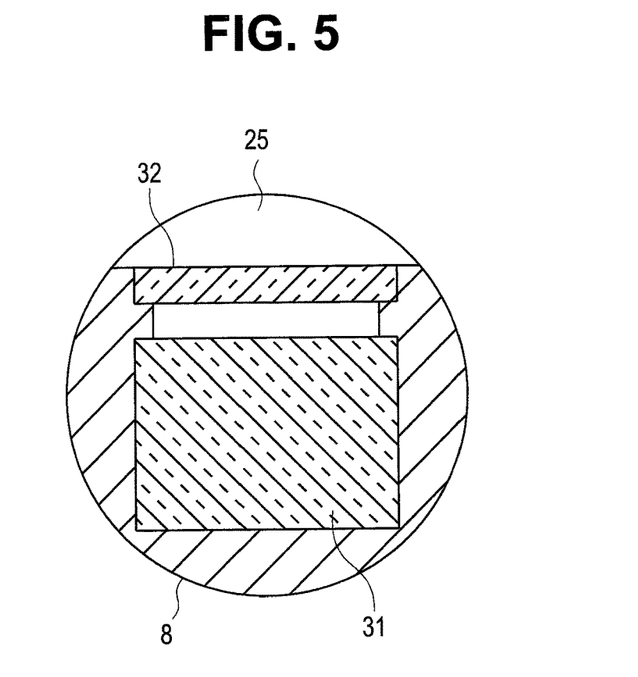
FIG. 5 is a cross-sectional view illustrating the configuration of the distal end portion taken along line V-V in FIG. 4, according to the aspect.
Figure 6:
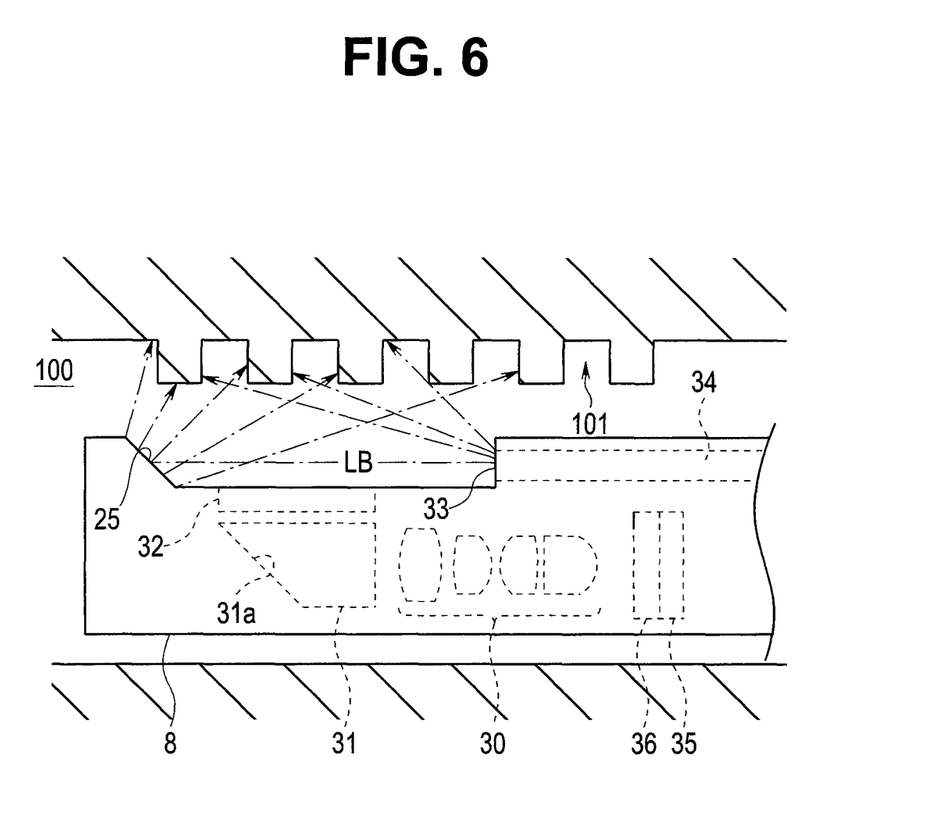
FIG. 6 is a schematic diagram illustrating the distal end portion inserted into a conduit, according to the aspect.

FIG. 1 is an external appearance configuration diagram of an endoscope apparatus according to an aspect, FIG. 2 is a perspective view illustrating a configuration of a distal end portion as viewed from a distal end side, FIG. 3 is a perspective view illustrating the configuration of the distal end portion as viewed from proximal end side, FIG. 4 is a cross-sectional view illustrating the configuration of the distal end portion, FIG. 5 is a cross-sectional view illustrating the configuration of the distal end portion taken along line V-V in FIG. 4, and FIG. 6 is a schematic diagram illustrating the distal end portion inserted into a conduit.

As illustrated in FIG. 1, an endoscope apparatus 1 is configured to include a main body section 2 that is a main unit, and a scope unit 3 that serves as an endoscope connected to the main body section 2. The main body section 2 includes a liquid crystal panel (hereinafter, abbreviated as LCD) 4 that is a display device on which an endoscope image, an operation menu, and the like are displayed. The LCD 4 is a display section that displays the endoscope image. The LCD 4 may include a touch panel.

The scope unit 3 includes an operation section 5, a universal cable 6 that connects the operation section 5 and the main body section 2, and an insertion section 7 including a flexible insertion tube. The scope unit 3 is detachably attachable to the main body section 2 through the universal cable 6.

A distal end portion 8 as an endoscope distal end portion is provided at a distal end of the insertion section 7, and a bending portion 9 is continuously provided on proximal end side of the distal end portion 8. An unillustrated image pickup device is incorporated in the distal end portion 8 as the endoscope distal end portion in this example.

Note that the image pickup device is an extremely-small electronic component, and includes, on a planar light receiving portion, a plurality of arranged elements each outputting an electric signal corresponding to entered light, at predetermined timing. For example, a type referred to as a CCD (charge-coupled device) sensor or a CMOS (complementary metal-oxide semiconductor) sensor, or other various kinds of types are typically applied to the image pickup device.

The operation section 5 includes various kinds of operation buttons such as a freeze button and a recording instruction button. Note that the scope unit 3 may include a configuration including an image guide fiber without the image pickup device.

A user operates the various kinds of operation buttons of the operation section 5, thereby picking up an image of an object, performing movie recording and still image recording, etc. Further, the user operates a bending lever 5a in vertical and horizontal (U/D/L/R) directions, thereby bending the bending portion 9 in a desired direction.

Moreover, in a case of a configuration in which the LCD 4 includes a touch panel, the user can operate the touch panel to instruct various operations of the endoscope apparatus 1.

Image data of the endoscope image acquired through image pickup is inspection data of an inspection object, and is recorded in a memory card 11 serving as a recording medium. The memory card 11 is detachably attachable to the main body section 2. Note that the image data is recorded in the memory card 11; however, the image data may be recorded in an unillustrated memory incorporated in the main body section 2.

Next, a configuration of the distal end portion 8 as the endoscope distal end portion according to the present embodiment is described below.

As illustrated in FIG. 2 and FIG. 3, the distal end portion 8 of the insertion section 7 of the scope unit 3 includes a substantially columnar shape, and is formed of a metal such as stainless steel.

An objective lens group 30 is incorporated in the distal end portion 8. A prism 31 serving as a shooting optical path conversion member is disposed forward (on distal end side) of the objective lens group 30.

The distal end portion 8 includes, at a side periphery, a plane part 21 that is parallel to a longitudinal axis X. An observation window 32 including a rectangular surface is disposed on the plane part 21. The observation window 32 is disposed to face one surface of the prism 31 incorporated in the distal end portion 8.

In other words, the scope unit 3 according to the present embodiment is a so-called side-viewing endoscope in which the observation window 32 of the distal end portion 8 is provided on the side part, and an observation visual field direction is orthogonal to an insertion axis (longitudinal axis X) of the insertion section 7.

Note that the scope unit 3 may be an oblique-viewing endoscope in which the observation visual field direction includes a predetermined angle with respect to the insertion axis (longitudinal axis X) of the insertion section 7. The visual field direction in the side viewing or the oblique viewing is defined by an angle of a reflection surface 31a of the prism 31 in this example.

The distal end portion 8 includes, at a wall part 22, an illumination window 33 that serves as an irradiation portion of illumination light. The wall part 22 is provided at a proximal end of the plane part 21 and is substantially perpendicular to the plane part 21. The illumination window 33 is an end surface that is obtained by cutting, with use of a diamond cutter or the like, a light guide bundle 34 that is inserted and disposed in the insertion section 7. Note that the illumination window 33 may include a configuration including an illumination lens.

A planar reflector 25 is disposed on the distal end portion 8. The reflector 25 is provided to include a predetermined angle θ (see FIG. 4) with respect to the longitudinal axis X so as to project forward from a distal end of the plane part 21.

In other words, the reflector 25 is disposed to face the illumination window 33 provided on the proximal end of the plane part 21, at a predetermined angle θ. Note that the predetermined angle θ of the reflector 25 with respect to the longitudinal axis X may be any angle as long as the predetermined angle θ is larger than 0 degrees and equal to or smaller than 90 degrees (0 degrees<θ≤90 degrees).

Further, the reflector 25 includes a substantially half-moon-shaped plane that includes an arc-shaped outer periphery along an outer shape of the distal end portion 8 (see FIG. 5). Furthermore, a surface of the reflector 25 has been subjected to mirror finishing, white coating, mirror finishing by aluminum deposition, or the like.

Furthermore, the reflector 25 is provided to stand obliquely-forward in an outer diameter direction from a position separated forward by a predetermined length (distance) L from the observation window 32, at a position out of effective angle of view of the observation image captured through the observation window 32 (see FIG. 4).

This eliminates inhibition of the visual field of the scope unit 3, and prevents harmful light reflected by the reflector 25 from entering the observation window 32, thereby preventing occurrence of halation, etc. Note that the distal end portion 8 includes an image pickup device 35. The image pickup device 35 includes a cover glass 36 that is disposed on a front surface on image side of the objective lens group 30.

The scope unit 3 including the above-described configuration according to the present embodiment is used for endoscope inspection by a user through insertion of the insertion section 7 into a pipe, an engine, or the like.

For example, as illustrated in FIG. 6, when a concave-convex part 101 on an observation surface of a conduit 100 is observed, illumination light LB is applied from rear (proximal end) side toward front (distal end) side because the illumination window 33 is provided on the rear side of the observation window 32.

Further, the illumination light LB outputted from the illumination window 33 is reflected by the reflector 25 that is disposed on the front side of the observation window 32, and the reflected illumination light is applied to an observation region of the concave-convex part 101 on obliquely rear side. Accordingly, the illumination light LB is applied also to rear side of a concave part of the concave-convex part 101 that is hidden and is difficult to be viewed in the related art, which improves observation property.

As described above, in the scope unit 3 according to the present embodiment, the reflector 25 that reflects the illumination light LB applied from the illumination window 33 is provided forward of the observation window 32 on the distal end portion 8. This causes the illumination light LB to be evenly applied also to a part where the illumination light LB does not reach in the related art and to the concave part that is hidden by the concave-convex part 101. As a result, the scope unit 3 is significantly improved in observation property as compared with the related art.

As described above, the scope unit 3 includes the configuration that is improved in observation property through suppression of occurrence of illumination unevenness by the illumination light LB in observation of screw threads of a pipe, rear side of an engine turbine, a common rail of an engine, etc. Moreover, the scope unit 3 reduces a part where the illumination light LB does not reach, which makes it possible to easily detect minute concave and convex on an inner surface of a fine pipe, etc.

Accordingly, the scope unit 3 according to the present embodiment includes the configuration that prevents occurrence of illumination unevenness due to, for example, a part where the illumination light LB in the observation direction does not reach and a hidden part, to improve the observation property.

Modifications

Note that the above-described configuration of the distal end portion 8 of the scope unit 3 is one aspect, and the distal end portion 8 of the scope unit 3 may include a configuration described in any of the following various modifications. In addition, the configurations of the respective modifications exemplified below may be combined in some cases.

First Modification

Figure 7:
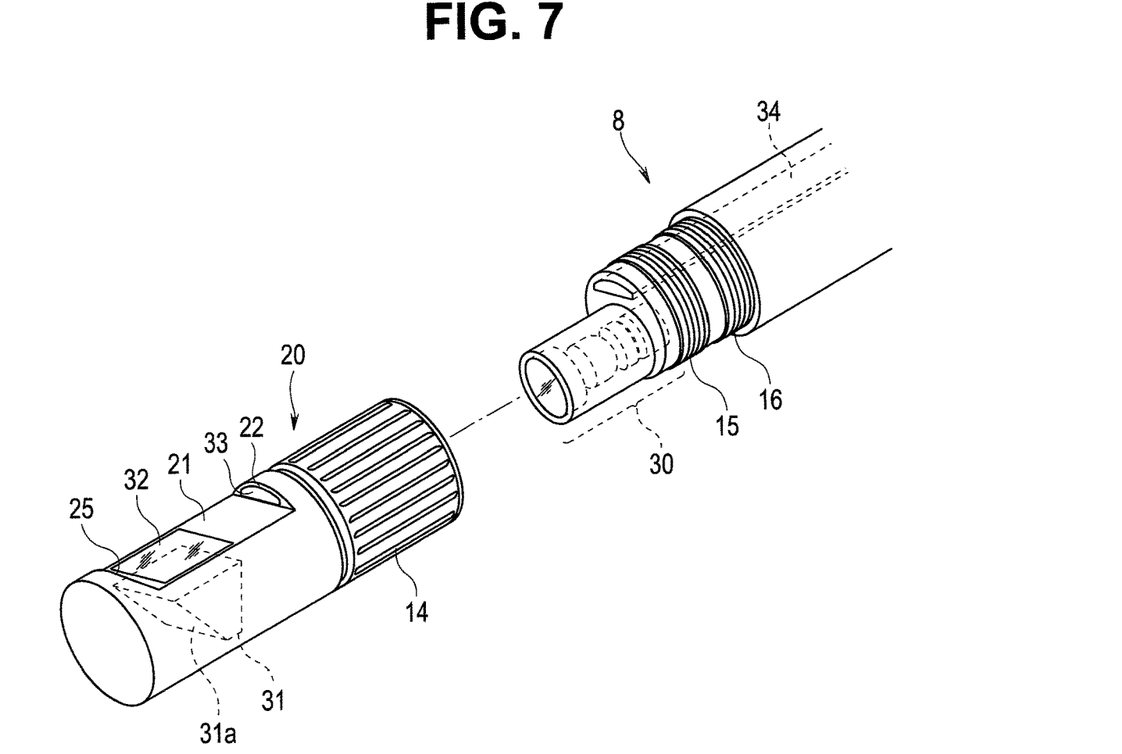
FIG. 7 is an exploded perspective view illustrating an optical adapter and a distal end portion of an insertion section, according to a first modification of the aspect.
Figure 8:
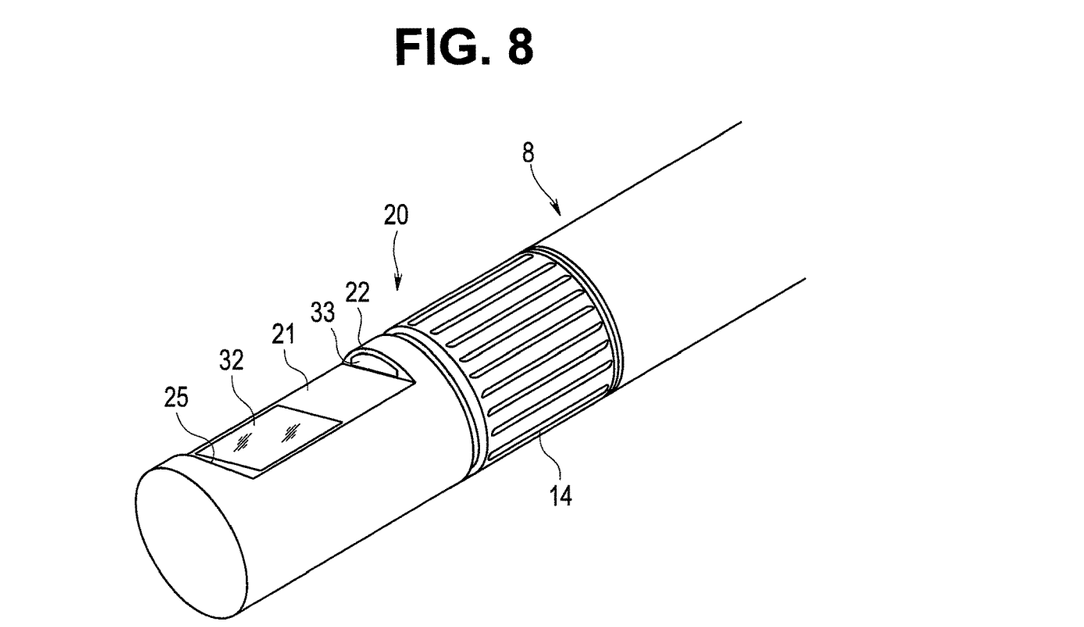
FIG. 8 is a perspective view illustrating a state where the optical adaptor is attached to the distal end portion of the insertion section, according to the first modification of the aspect.

FIG. 7 is an exploded perspective view illustrating an optical adaptor and a distal end portion of an insertion section according to a first modification, and FIG. 8 is a perspective view of a state where the optical adaptor is attached to the distal end portion of the insertion section according to the first modification.

As illustrated in FIG. 7 and FIG. 8, an optical adaptor 20 for side viewing or oblique viewing that is detachably attachable to the distal end portion 8 may be prepared, and the reflector 25 may be provided on the optical adaptor 20.

Note that the optical adaptor 20 includes a retaining ring 14 at a proximal end part. The retaining ring 14 is attached or detached by screwing to/from male screw parts 15 and 16 provided on the distal end portion 8, which allows the optical adaptor 20 to be detachably attachable.

With such a configuration, the optical adaptor for front viewing and the optical adaptor 20 for side viewing or oblique viewing is selectively mountable to the scope unit 3 depending on various inspection objects.

Second Modification

Figure 9:
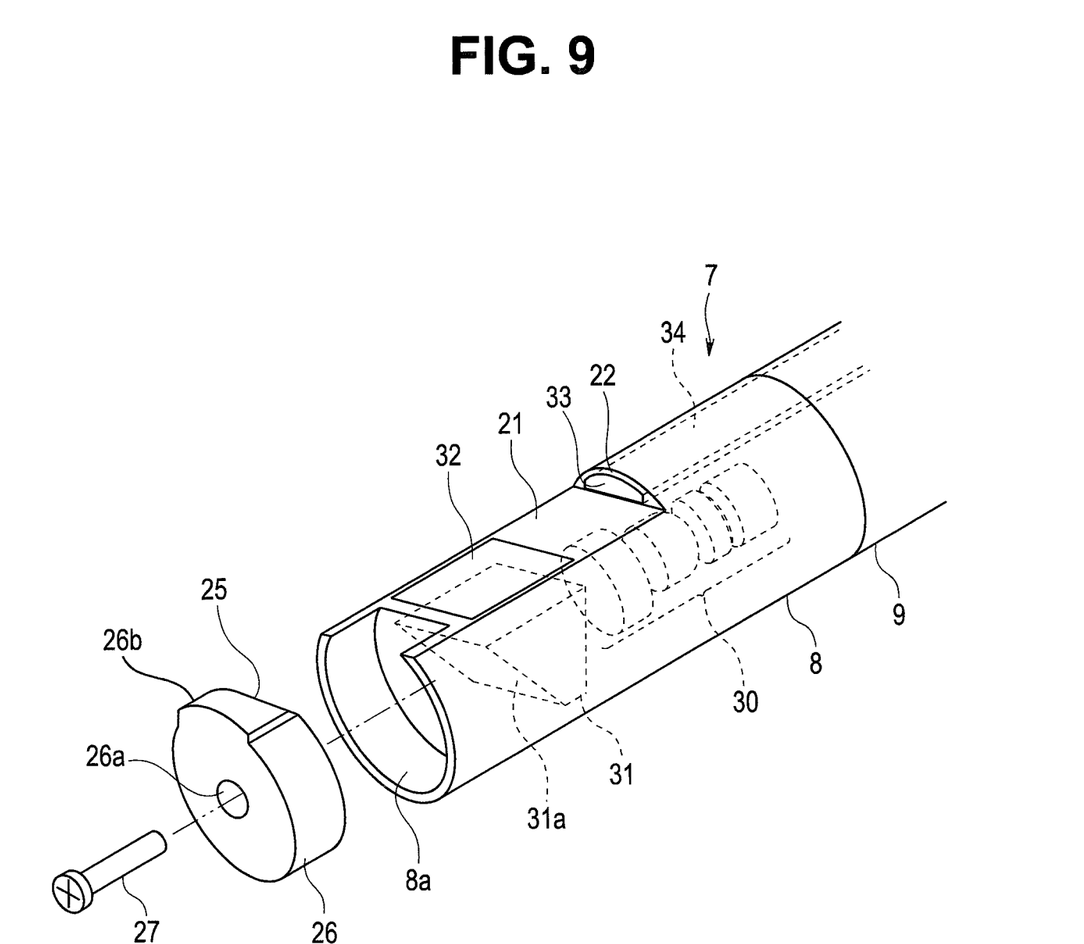
FIG. 9 is an exploded perspective view illustrating a distal end portion of an insertion section to which a reflection adapter is to be attached, according to a second modification of the aspect.
Figure 10:
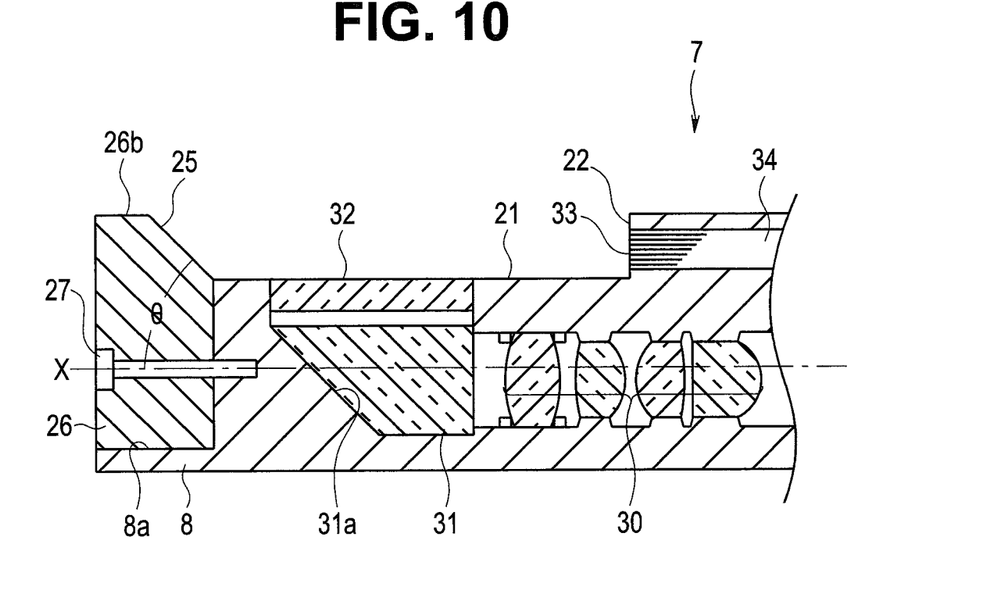
FIG. 10 is a cross-sectional view illustrating the distal end portion of the insertion section attached with the reflection adapter, according to the second modification of the aspect.
Figure 11:
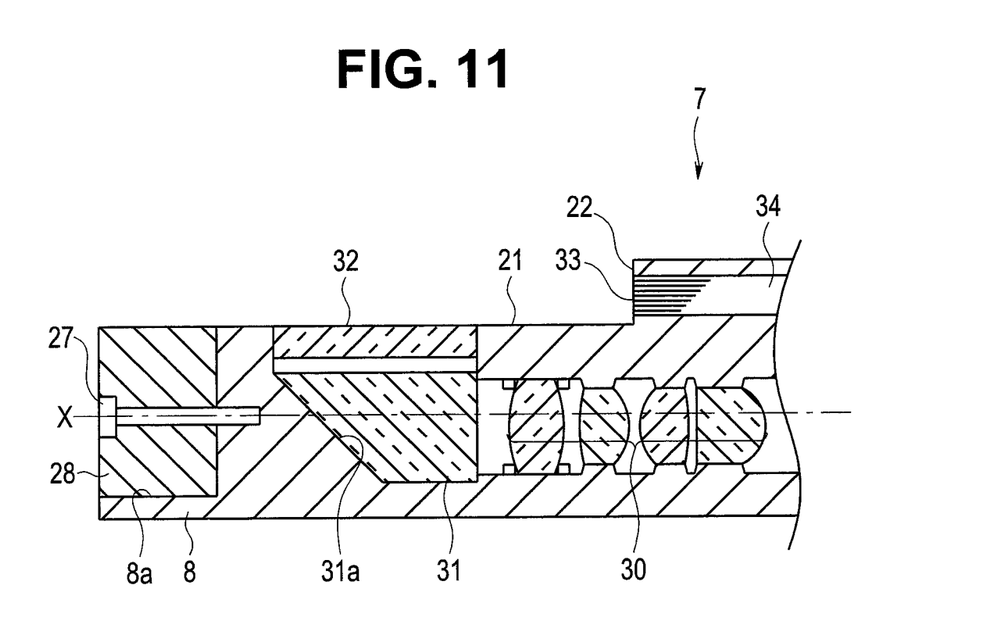
FIG. 11 is a cross-sectional view illustrating the distal end portion of the insertion section attached with an adapter, according to the second modification of the aspect.

FIG. 9 is an exploded perspective view illustrating a distal end portion of an insertion section to which a reflection adaptor is to be attached according to a second modification, FIG. 10 is a cross-sectional view of the distal end portion of the insertion section attached with the reflection adaptor according to the second modification, and FIG. 11 is a cross-sectional view illustrating the distal end portion of the insertion section attached with an adaptor according to the second modification.

As illustrated in FIG. 9 and FIG. 10, a configuration of a reflection adaptor 26 that includes the reflector 25 and is detachably attachable to the distal end portion 8 may be used.

The reflection adaptor 26 is fitted to a concave part 8*a* provided on a distal end part of the distal end portion 8, and is fixed to the distal end portion 8 through insertion of a screw 27 into a screw hole 26*a* provided at a substantially center part of the reflection adaptor 26.

Note that the reflection adaptor 26 includes a substantially disc-block shape including a convex part 26*b* provided with the reflector 25, and the cylindrical concave part 8*a* that is partially opened in a shape similar to the shape of the reflection adaptor 26 is provided at the distal end portion 8.

In the scope unit 3, such a configuration makes it possible to change the reflection angle of the illumination light LB reflected by the reflector 25 to any of various desired reflection angles by replacing the reflection adaptor 26 attached to the distal end portion 8 with a reflection adaptor 26 having a different predetermined angle θ with respect to the longitudinal axis X of the reflector 25.

Further, as illustrated in FIG. 11, an adaptor 28 not including the reflector 25 may be attached to the distal end portion 8, and it is possible to selectively attach and use the reflection adaptor 26 or the adaptor 28 depending on various inspection objects of the scope unit 3.

Third Modification

Figure 12:
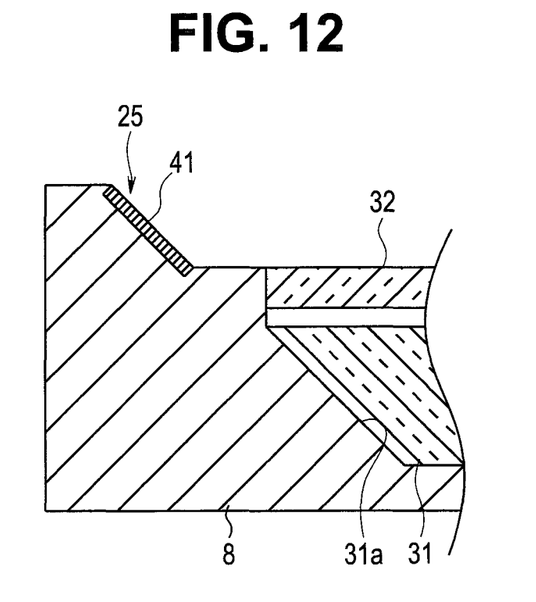
FIG. 12 is a partial cross-sectional view illustrating a distal end portion of an insertion section in which a mirror plate is provided on a reflector, according to a third modification of the aspect.
Figure 13:
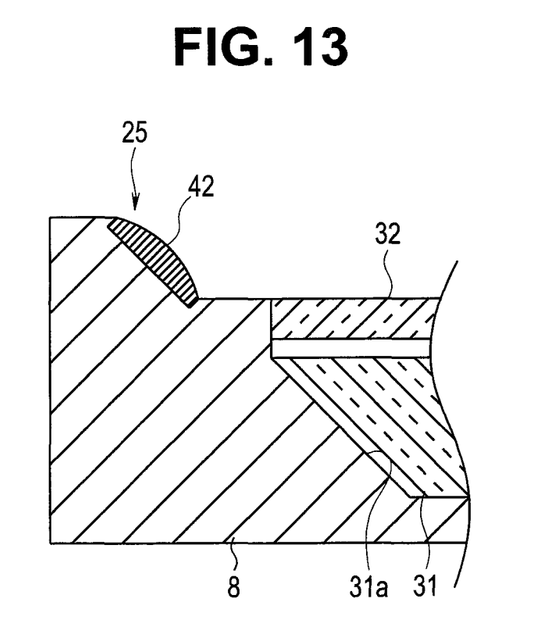
FIG. 13 is a partial cross-sectional view illustrating the distal end portion of the insertion section in which a convex mirror plate is provided on the reflector, according to the third modification of the aspect.
Figure 14:
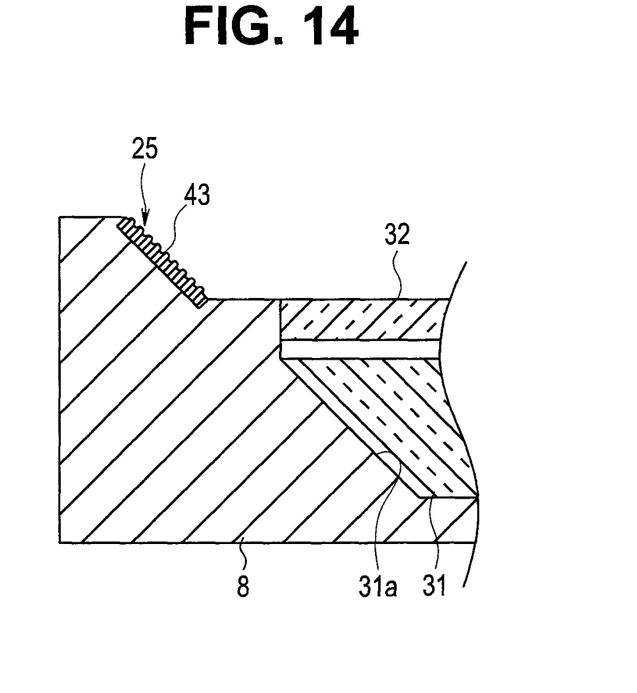
FIG. 14 is a partial cross-sectional view illustrating the distal end portion of the insertion section in which an uneven light diffusion plate is provided on the reflector, according to the third modification of the aspect.
Figure 15:
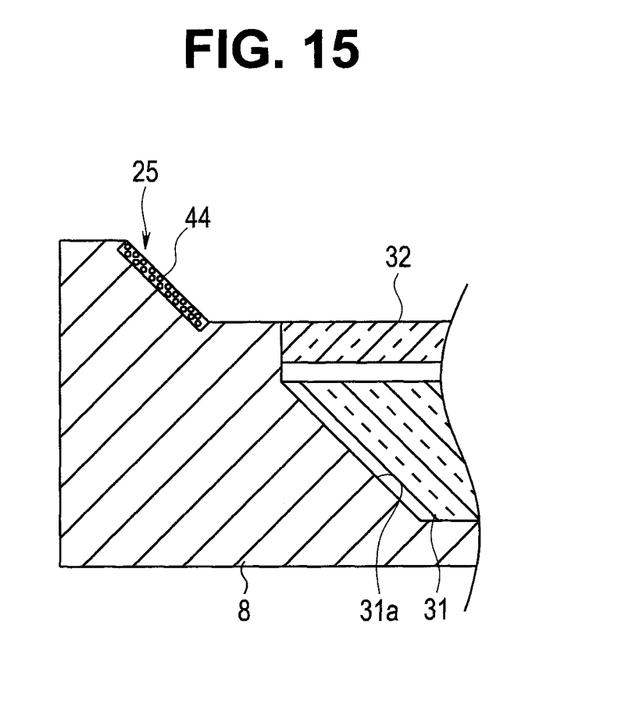
FIG. 15 is a partial cross-sectional view illustrating the distal end portion of the insertion section in which a light diffusion plate with glass beads is provided on the reflector, according to the third modification of the aspect.

FIG. 12 is a partial cross-sectional view illustrating a distal end portion of an insertion section in which a mirror plate is provided on a reflector according to a third modification, FIG. 13 is a partial cross-sectional view illustrating the distal end portion of the insertion section in which a convex mirror plate is provided on the reflector according to the third modification, FIG. 14 is a partial cross-sectional view illustrating the distal end portion of the insertion section in which an uneven light diffusion plate is provided on the reflector according to the third modification, and FIG. 15 is a partial cross-sectional view illustrating the distal end portion of the insertion section in which a light diffusion plate with glass beads is provided on the reflector according to the third modification.

A mirror plate 41 may be provided on the reflector 25 of the distal end portion 8 as illustrated in FIG. 12, or a convex mirror plate 42 including a convex surface may be provided on the reflector 25 of the distal end portion 8 as illustrated in FIG. 13. Further, a light diffusion plate 43 including a plurality of unevennesses may be provided on the reflector 25 of the distal end portion 8 as illustrated in FIG. 14, or a light diffusion plate 44 that includes a plurality of glass beads fixed with a transparent adhesive may be provided on the reflector 25 of the distal end portion 8 as illustrated in FIG. 15.

Fourth Modification

Figure 16:
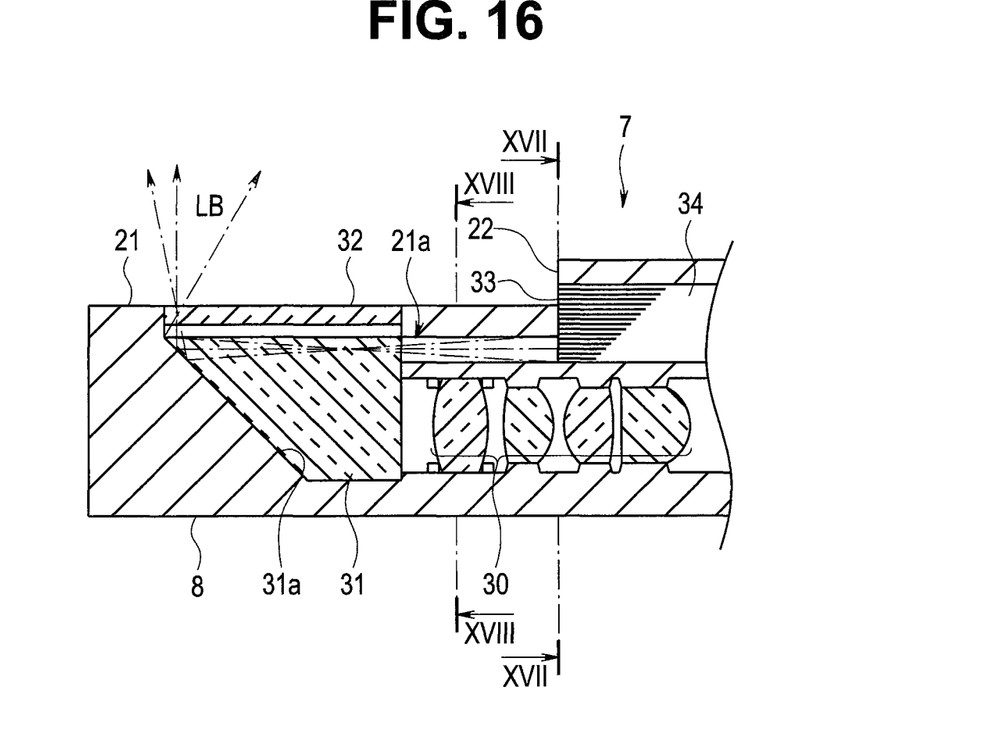
FIG. 16 is a cross-sectional view illustrating a distal end portion of an insertion section, according to a fourth modification of the aspect.
Figure 17:
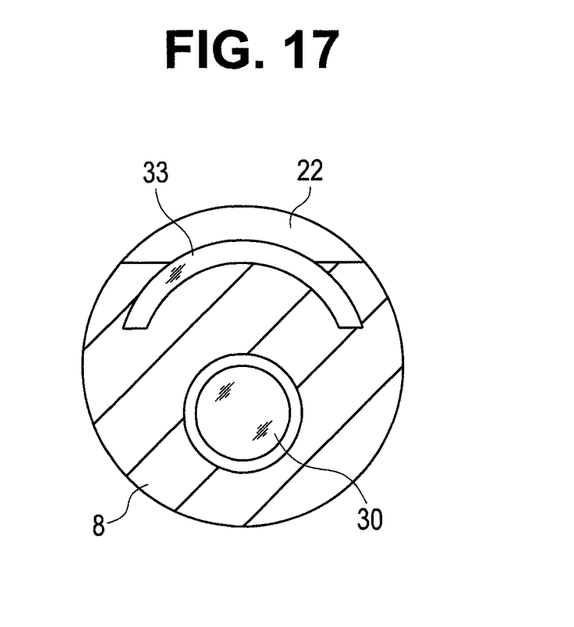
FIG. 17 is a cross-sectional view illustrating the distal end portion taken along line XVII-XVII in FIG. 16, according to the fourth modification of the aspect.
Figure 18:
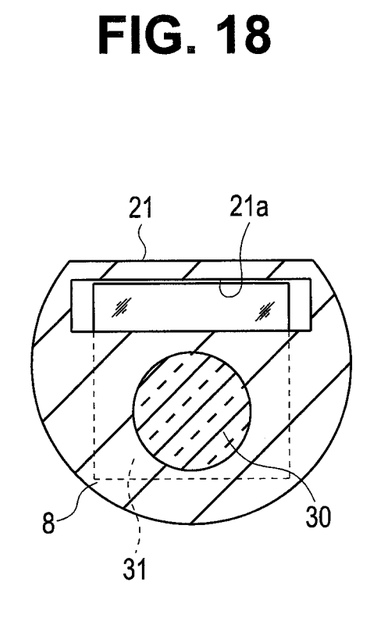
FIG. 18 is a cross-sectional view illustrating the distal end portion taken along line XVIII-XVIII in FIG. 16, according to the fourth modification of the aspect.
Figure 19:
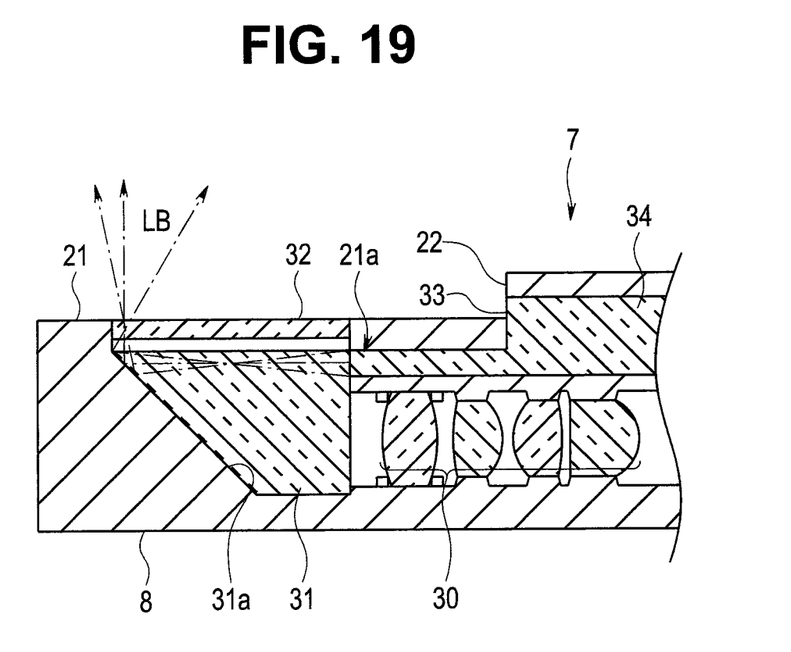
FIG. 19 is a cross-sectional view illustrating a distal end portion of an insertion portion in another form, according to the fourth modification of the aspect.

FIG. 16 is a cross-sectional view illustrating a distal end portion of an insertion section according to a fourth modification, FIG. 17 is a cross-sectional view illustrating the distal end portion taken along line XVII-XVII in FIG. 16 according to the fourth modification, FIG. 18 is a cross-sectional view illustrating the distal end portion taken along line XVIII-XVIII in FIG. 16 according to the fourth modification, and FIG. 19 is a cross-sectional view illustrating the distal end portion of the insertion section in another form according to the fourth modification.

As illustrated in FIG. 16 and FIG. 17, in the distal end portion 8 in the example, both end parts of the light guide bundle 34 including an arc-shaped cross-section are embedded. As illustrated in FIG. 18, a hole part 21*a* is provided on the distal end portion 8 such that the illumination light LB outputted from the both end parts of the illumination window 33 of the light guide bundle 34 enters the prism 31.

Such a configuration allows the reflection surface 31*a* of the prism 31 to be substituted for a reflector reflecting the illumination light LB without necessity of providing the reflector 25 on the distal end portion 8, which makes it possible to apply the illumination light LB obliquely to the concave-convex part 101 (see FIG. 6) that is not illustrated in FIG. 16.

Note that, as illustrated in FIG. 19, the hole part 21*a* of the distal end portion 8 may be filled with the light guide bundle 34.

Fifth Modification

Figure 20:
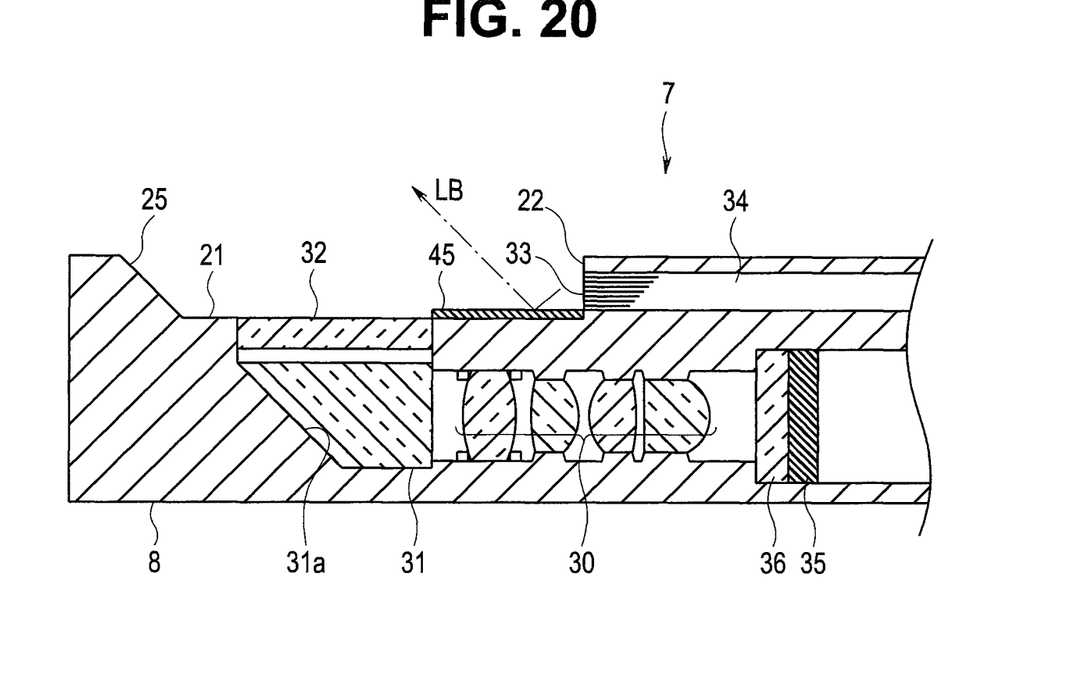
FIG. 20 is a cross-sectional view illustrating a distal end portion in which a reflection surface is provided on a plane part, according to a fifth modification of the aspect.
Figure 21:
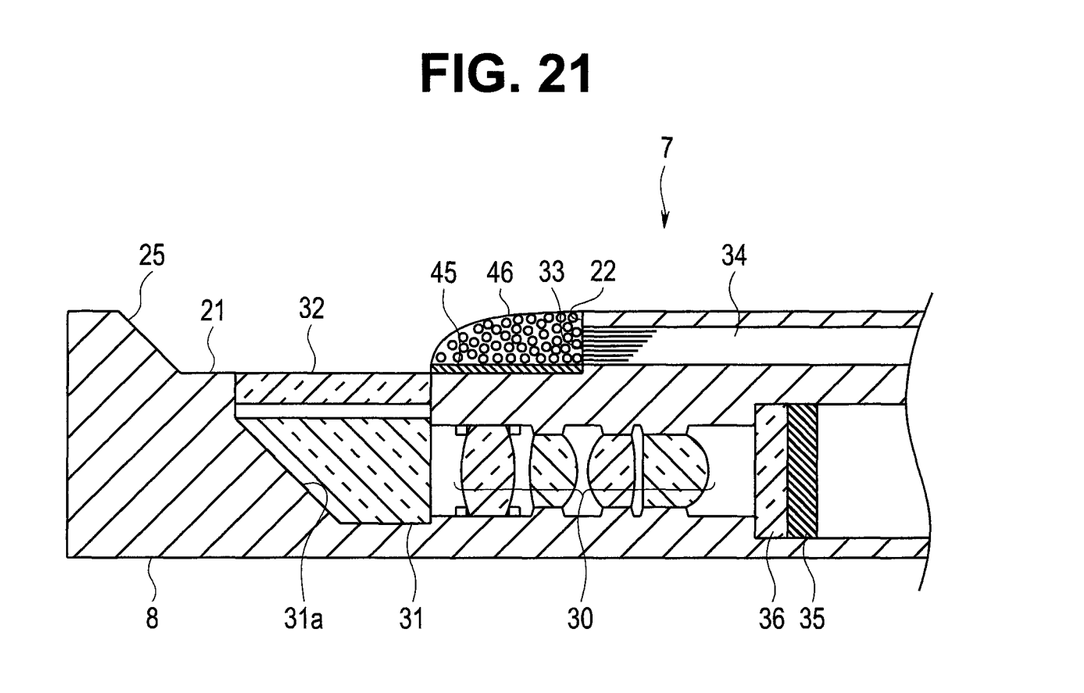
FIG. 21 is a cross-sectional view illustrating the distal end portion in which a convex light scattering part is provided on the reflection surface, according to the fifth modification of the aspect.
Figure 22:
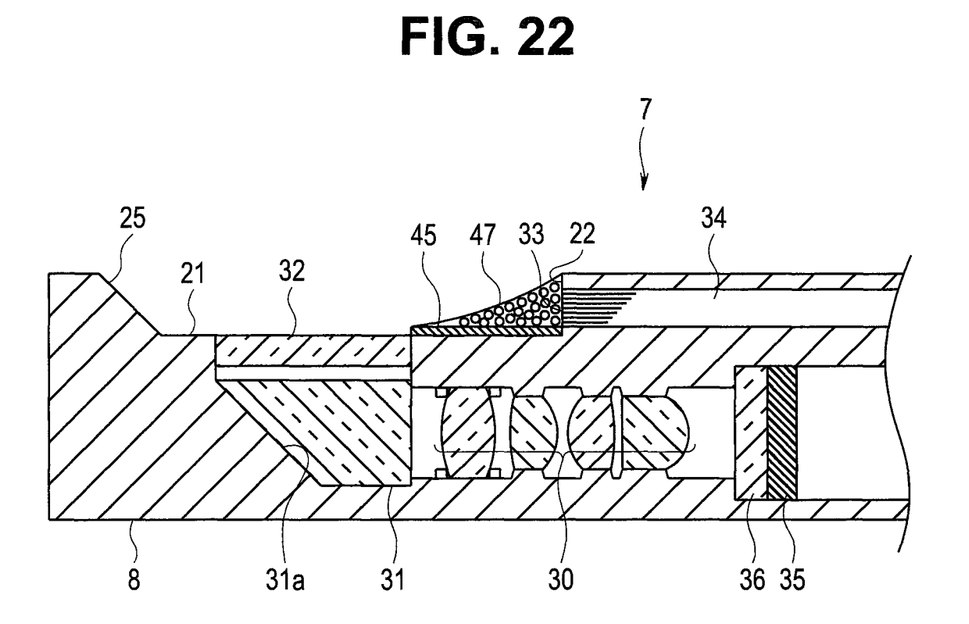
FIG. 22 is a cross-sectional view illustrating the distal end portion in which a concave light scattering part is provided on the reflection surface, according to the fifth modification of the aspect.
Figure 23:
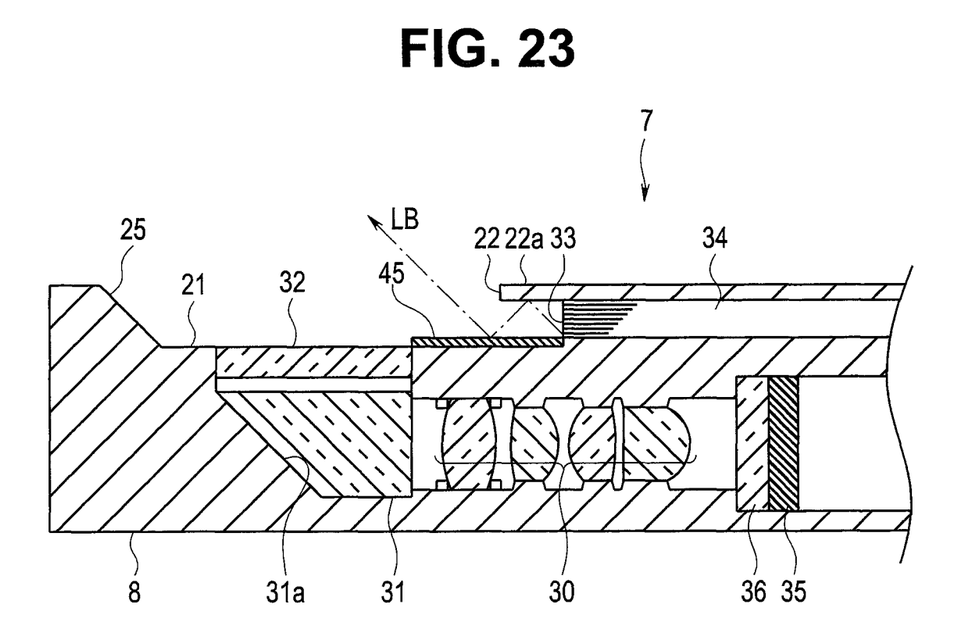
FIG. 23 is a cross-sectional view illustrating the distal end portion in which an eaves part is provided on an illumination window, according to the fifth modification of the aspect.

FIG. 20 is a cross-sectional view illustrating a distal end portion in which a reflection surface is provided on a plane part according to a fifth modification, FIG. 21 is a cross-sectional view illustrating the distal end portion in which a convex light scattering part is provided on the reflection surface according to the fifth modification, FIG. 22 is a cross-sectional view illustrating the distal end portion in which a concave light scattering part is provided on the reflection surface according to the fifth modification, and FIG. 23 is a cross-sectional view illustrating the distal end portion in which an eaves part is provided on the illumination window according to the fifth modification.

As illustrated in FIG. 20, a reflection surface 45 coated with metal plating that reflects the illumination light LB from the illumination window 33 may be provided on the plane part 21 between the illumination window 33 and the observation window 32. In addition, as illustrated in FIG. 21, a concave light scattering part 46 in which a plurality of glass beads scattering the illumination light LB from the illumination window 33 are put and fixed with a transparent adhesive may be provided on the reflection surface 45. Alternatively, a concave light scattering part 47 may be provided on the reflection surface 45 as illustrated in FIG. 22.

Furthermore, as illustrated in FIG. 23, an eaves part 22*a* may be provided so as to extend forward from the illumination window 33, and the illumination light LB from the illumination window may be reflected on an inner surface of the eaves part 22*a*, and the reflected illumination light may accordingly enter the reflection surface 45.

The invention described in the above-described embodiment is not limited to the embodiment and the modifications, and may be additionally variously modified in implementation without departing from the scope of the invention. Further, the above-described embodiment includes the invention in various stages, and various inventions may be extracted through appropriate combinations of the plurality of disclosed components.

For example, even if some components are deleted from all the components described in the embodiment, a configuration with the components deleted may be extracted as the invention if such a configuration can solve a problem to be solved by the invention and provides the effects of the invention.

The present invention makes it possible to provide the endoscope distal end portion, the endoscope, and the optical adaptor that each include the observation direction including an angle with respect to the insertion direction, and apply the illumination light to the observation site where the illumination light does not reach in the related art, thereby being improved in observation property.

What is claimed is:

1. An endoscope distal end portion having a longitudinal axis and being provided at a distal end of an insertion section, the endoscope distal end portion comprising:
   an observation window provided on a side with respect to an insertion direction of the insertion section, the observation window being configured to optically guide an object image to one or more lenses disposed in the distal end;
   an illumination window disposed proximally relative to the observation window, the illumination window being configured to output illumination light from within the distal end; and
   a reflector disposed distally relative to the observation window, the reflector being arranged at a predetermined angle with respect to the longitudinal axis, the reflector being configured to reflect the illumination light outputted from the illumination window to an observation region proximal to the reflector.

2. The endoscope distal end portion according to claim 1, wherein the reflector is detachably attachable.

3. The endoscope distal end portion according to claim 1, wherein the reflector includes a mirror plate.

4. The endoscope distal end portion according to claim 3, wherein the mirror plate includes a convex surface.

5. The endoscope distal end portion according to claim 1, wherein the reflector includes a light diffusion plate.

6. An endoscope comprising:
   the insertion section; and
   the endoscope distal end portion according to claim 1 provided at the distal end of the insertion section.

* * * * *